(12) United States Patent
Maruyama (10) Patent No.: US 9,089,263 B2
(45) Date of Patent: Jul. 28, 2015

(54) ENDOSCOPE AND INSTRUMENT LIFTING OPERATION DEVICE FOR THE SAME

(75) Inventor: Yoshinori Maruyama, Saitama (JP)

(73) Assignee: HOYA CORPORATION, Tokyo (JP)

( * ) Notice: Subject to any disclaimer, the term of this patent is extended or adjusted under 35 U.S.C. 154(b) by 643 days.

(21) Appl. No.: 12/880,570

(22) Filed: Sep. 13, 2010

(65) Prior Publication Data

US 2011/0077461 A1    Mar. 31, 2011

(30) Foreign Application Priority Data

Sep. 30, 2009  (JP) ................................. 2009-225832

(51) Int. Cl.
   *A61B 1/018*    (2006.01)
   *A61B 1/00*     (2006.01)
   *A61B 1/005*    (2006.01)
   *G02B 23/24*    (2006.01)

(52) U.S. Cl.
   CPC ............... *A61B 1/018* (2013.01); *A61B 1/0052* (2013.01); *A61B 1/0057* (2013.01); *A61B 1/00098* (2013.01); *A61B 1/00133* (2013.01); *G02B 23/2476* (2013.01)

(58) Field of Classification Search
   USPC .......... 600/106, 107, 146–150; 604/523–528
   See application file for complete search history.

(56) References Cited

U.S. PATENT DOCUMENTS

| | | | |
|---|---|---|---|
| 5,507,717 A * | 4/1996 | Kura et al. ............... | 600/146 |
| 6,582,357 B2 | 6/2003 | Ouchi et al. | |
| 6,656,111 B2 | 12/2003 | Fujii et al. | |
| 6,673,012 B2 | 1/2004 | Fujii et al. | |
| 6,814,728 B2 | 11/2004 | Ouchi | |
| 6,878,108 B2 | 4/2005 | Ouchi | |
| 7,087,010 B2 | 8/2006 | Ootawara et al. | |
| 7,341,555 B2 * | 3/2008 | Ootawara et al. ............ | 600/106 |
| 7,794,392 B2 | 9/2010 | Maruyama | |
| 7,828,725 B2 | 11/2010 | Maruyama | |
| 7,846,089 B2 | 12/2010 | Maruyama | |

(Continued)

FOREIGN PATENT DOCUMENTS

| | | |
|---|---|---|
| JP | 49-74788 | 6/1974 |
| JP | 53-20945 | 6/1978 |
| JP | 62-84402 | 5/1987 |
| JP | 7-148104 | 6/1995 |
| JP | 9-84757 | 3/1997 |
| JP | 10-5174 | 1/1998 |
| JP | 11-28184 | 2/1999 |
| JP | 2002-34905 | 2/2002 |
| JP | 2003-245248 | 9/2003 |

OTHER PUBLICATIONS

Japan Office action, dated Aug. 6, 2013 along with an english translation thereof.

*Primary Examiner* — Thomas J Sweet
*Assistant Examiner* — Kevin G Barry, III
(74) *Attorney, Agent, or Firm* — Greenblum & Bernstein, P.L.C.

(57) ABSTRACT

An instrument lifting operation device including: an operation wire drawing mechanism configured to draw an proximal end of an operation wire connected to an instrument lifting piece; and a braking mechanism configured to restrict movement of the operation wire toward the tip side, wherein the braking mechanism includes: a fixed wall; and a spring arranged to be able to rotate about an axis together with an instrument lifting operation member in a state where the spring is elastically pressed against an inner circumferential surface of the fixed wall. When the instrument lifting operation member is operated to rotate about the axis, the wire coupling member rotates about the axis and the operation wire moves forward and backward in a state where the spring contacts and slides on the inner circumferential surface of the fixed wall to generate frictional resistance at a contacting part.

14 Claims, 8 Drawing Sheets

(56) References Cited

U.S. PATENT DOCUMENTS

| | | |
|---|---|---|
| 2002/0091303 A1 | 7/2002 | Ootawara et al. |
| 2005/0049455 A1 | 3/2005 | Ootawara et al. |
| 2005/0203336 A1* | 9/2005 | Seki et al. ............... 600/101 |
| 2006/0041190 A1 | 2/2006 | Sato |
| 2006/0100484 A1* | 5/2006 | Maeda et al. ............. 600/146 |
| 2007/0255102 A1 | 11/2007 | Maruyama |
| 2007/0255104 A1* | 11/2007 | Maruyama ................ 600/148 |
| 2008/0319263 A1 | 12/2008 | Maruyama |
| 2009/0182196 A1* | 7/2009 | Kefer ........................ 600/114 |

\* cited by examiner

ENDOSCOPE AND INSTRUMENT LIFTING OPERATION DEVICE FOR THE SAME

BACKGROUND OF THE INVENTION

The present invention relates to an instrument lifting operation device for an endoscope.

Endoscopes provided with an instrument lifting piece for controlling the protruding direction of the tip of a treatment instrument inserted into an instrument-insertion channel have been used. In such an endoscope, an instrument lifting operation device is provided in an operation unit to be operated by an operator. The instrument lifting operation device serves to remotely control the instrument lifting piece from the operation unit to which a proximal end of an insertion unit is connected.

In the instrument lifting operation device, an operation wire drawing mechanism for manually drawing a proximal end of an operation wire whose tip is connected to the instrument lifting piece is provided. In the state where the tip of the treatment instrument is lifted by the instrument lifting piece, a force for restoring the instrument lifting piece to an original state acts on the instrument lifting pieces from the treatment instrument.

In this case, when the operator releases the operator's finger from an operation member of the operation wire drawing mechanism, the operation wire moves back to the tip side of the operation wire by a drawing force acting on the operation wire from the instrument lifting piece, and thereby the instrument lifting pieces is restored to the state of not lifting the instrument lifting piece as described in Japanese Patent Provisional Publications No. H9-84757A and 2003-245248A.

In view of such a problem, Japanese Utility Model Provisional Publication No. S49-74788U (hereafter, referred to as JP S49-74788U) discloses a configuration where a braking mechanism for restring movement of the operation wire toward the tip side caused by a drawing force applied from an instrument lifting piece is provided in an operation unit.

SUMMARY OF THE INVENTION

In the braking mechanism described in JP S49-74788U, a sliding plate is arranged to face a friction plate arranged to be orthogonal to an rotation axis, and the sliding plate is constantly pressed against the friction plate by a spring like a coned disc spring. As a result, movement of the operation wire to move back to the tip side can be restricted by the frictional resistance caused between the frictional plate and the sliding plate.

However, in the configuration described in JP S49-74788U, the frictional plate, the sliding plate and the sprig are stacked to have a sandwich-like structure. Therefore, the configuration of JP S49-74788U requires a relatively large space both in the radial direction and in the thickness direction. Such a configuration may badly affect arrangement of other operation mechanisms (e.g., a bending operation mechanism) in the operation unit.

Since the braking mechanism of the instrument lifting operation device is required to have a function of maintaining a stationary state of the operation wire, the barking mechanism needs to have a static frictional resistance of a certain level or more. However, the braking mechanism described in JP S49-74788U causes a relatively large amount of dynamic frictional resistance in addition to the static frictional resistance. Therefore, the strength of the operation force for drawing the operation wire from the operation unit side to lift the tip of the treatment instrument becomes increases. As a result, operability of the endoscope deteriorates.

The present invention is advantageous in that it provides an instrument lifting operation device for an endoscope configured to be effectively arranged in an operation unit without interfering with another mechanism to be provided in the operation unit, to be able to reduce the dynamic frictional resistance relative to the static frictional resistance, and thereby to enable an operator to smoothly conduct an operation for lifting a treatment instrument by a small force.

According to an aspect of the invention, there is provided an instrument lifting operation device for an endoscope for remotely controlling, from an operation unit connected to a proximal end of an insertion unit, an instrument lifting piece movably arranged on a tip side of the insertion unit of the endoscope. The instrument lifting operation device includes: an operation wire drawing mechanism configured to draw, in response to a manual operation, an proximal end of an operation wire whose tip is connected to the instrument lifting piece; and a braking mechanism configured to restrict movement of the operation wire toward the tip side by a drawing force applied to the operation wire from the instrument lifting piece. The operation wire drawing mechanism and the breaking mechanism are arranged in the operation unit of the endoscope. In this configuration, the operation wire drawing mechanism includes: an instrument lifting operation member which is rotatable about an axis; and a wire coupling member to which the proximal end of the operation wire is connected, the wire coupling member being arranged to be rotated about the axis by the instrument lifting operation member. The braking mechanism includes: a fixed wall fixedly arranged in the operation unit to have an shape of an arc having a center corresponding to the axis; a spring arranged to be able to rotate about the axis together with the instrument lifting operation member in a state where the spring is elastically pressed against an inner circumferential surface of the fixed wall. When the instrument lifting operation member is operated to rotate about the axis, the wire coupling member rotates about the axis and the operation wire moves forward and backward in a state where the spring contacts and slides on the inner circumferential surface of the fixed wall to generate frictional resistance at a contacting part of the spring and the inner circumferential surface of the fixed wall.

With this configuration, it becomes possible to effectively arrange the instrument lifting operation device in the operation unit without interfering with another mechanism to be provided in the operation unit. Furthermore, it becomes possible to reduce the dynamic frictional resistance relative to the static frictional resistance, and thereby to enable an operator to smoothly conduct an operation for lifting a treatment instrument by a small force.

In at least one aspect, the spring may include: a fixed end fixed to a rotation member arranged to rotate about the axis together with the instrument lifting operation member; and a free end which contacts and slides on the inner circumferential surface of the fixed wall. In this case, the spring is configured such that a contacting projection is formed to locally protrude at a portion of the free end of the spring and to contact and slide on the inner circumferential surface of the fixed wall.

In at least one aspect, the instrument lifting operation member and the contacting projection of the spring may be arranged substantially in a same direction when viewed from a position of the axis.

In at least one aspect, a lubricant is applied to the contacting part of the spring and the inner circumferential surface of the fixed wall.

In at least one aspect, the lubricant is grease.

According to another aspect of the invention, there is provided an endoscope, comprising: an insertion unit; an operation unit connected to a proximal end of the insertion unit; and the above described instrument lifting operation device configured to remotely control, from the operation unit, an instrument lifting piece movably arranged on a tip side of the insertion unit.

DETAILED DESCRIPTION OF THE EMBODIMENTS

Hereinafter, an embodiment according to the invention is described with reference to the accompanying drawings.

Figure 2:
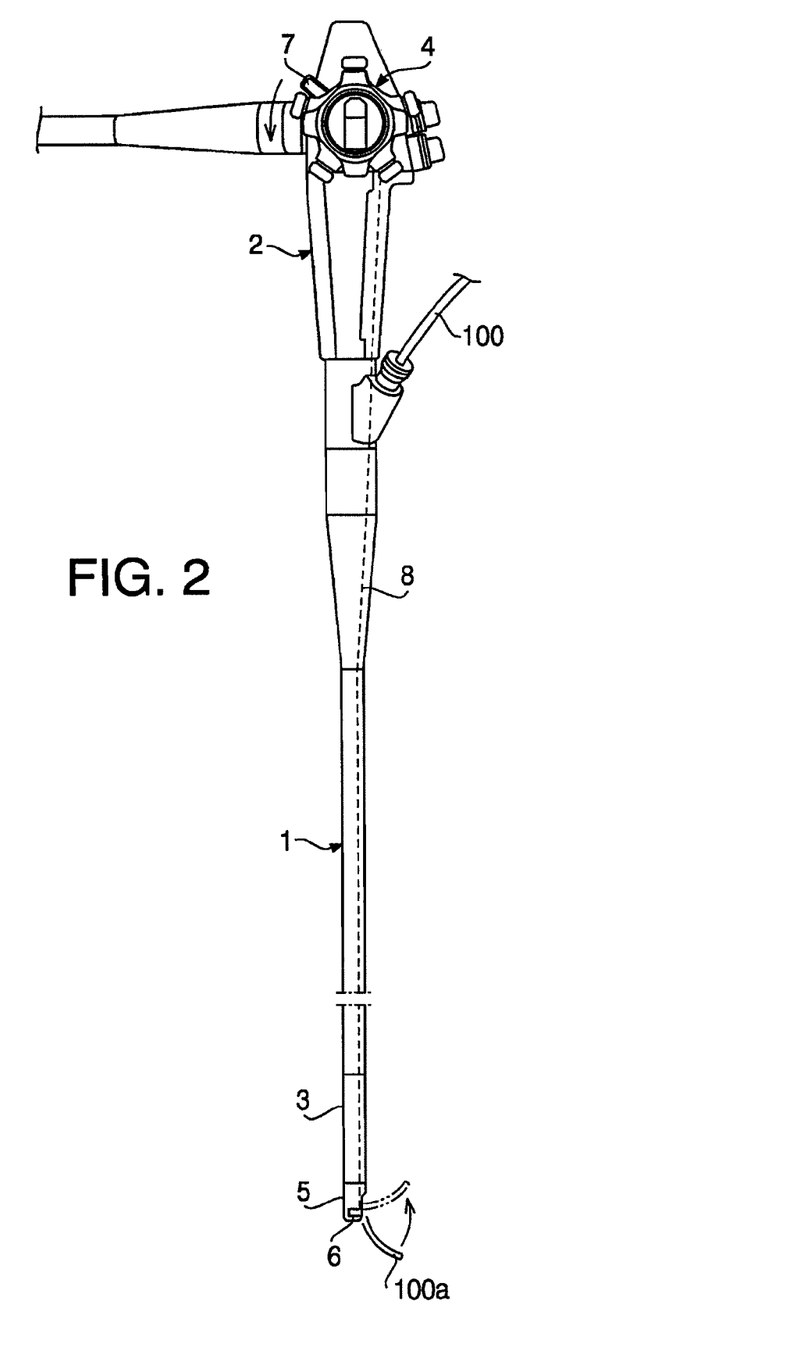
FIG. 2 illustrates an outer appearance of the entire configuration of an endoscope according an embodiment of the invention.

FIG. 2 illustrates an entire configuration of an endoscope. In the configuration shown in FIG. 2, a proximal end of an elastic insertion tube 1 having elasticity is connected to a lower end of an operation unit 2, and a bending part 3 connected to a tip end of the elastic insertion tube 1 is configured to be bent at a desired angle in a desired direction through remote control from a bending operation device 4 provided on the operation unit 2.

Reference number 5 represents a tip part body 5 which is connected to the tip of the bending part 3 to form a tip part of an insertion unit. The insertion unit is formed of the elastic insertion tube 1, the bending part 3 and the tip part body 5. In the insertion unit (i.e., in the elastic insertion tube 1, the bending part 3 and the tip part body 5), an instrument-inserting channel (not shown) is arranged so that a tip part 100a of a treatment instrument 100 inserted into the instrument-inserting channel protrudes from an instrument protrusion hole formed in the tip part body 5.

Inside the instrument protrusion hole of the tip part body 5, an instrument lifting piece 6 is accommodated to be able to swing, and a tip of an operation wire 8 is connected to the instrument lifting piece 6. In this configuration, by manually operating an instrument lifting operation lever 7 arranged in the operation unit 2, the operator is able to remotely control, through the operation wire 8, the instrument lifting piece 6 to swing, and thereby to control the protruding direction of the tip part 100a of the treatment instrument 100 which protrudes from the tip part body 5.

Specifically, in the state where the operation wire 8 has been pressed from the operation unit 2 side, the tip part 100a of the treatment instrument 100 protrudes obliquely to the front side from the tip part body 5 as indicated by a solid line in FIG. 2. On the other hand, when the operation wire 8 is drawn from the operation unit 2 side, the instrument lifting piece 6 is lifted and thereby the tip part 100a of the treatment instrument 100 is brought to the state shown by a double chain line in FIG. 2.

Figure 1:
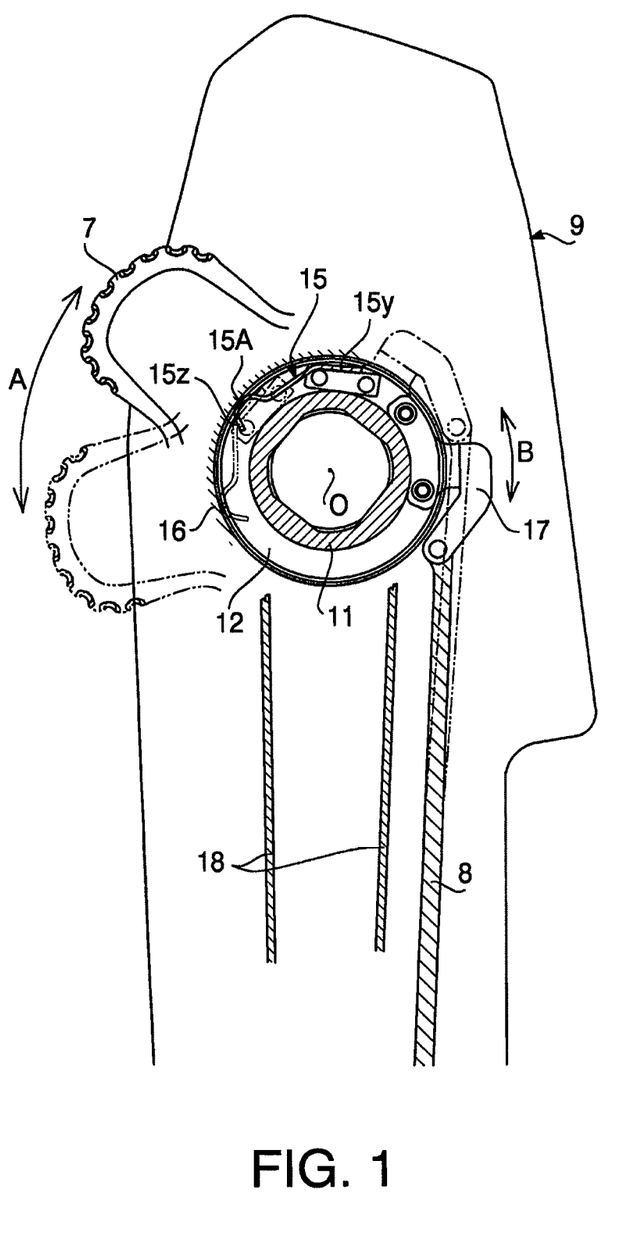
FIG. 1 is a combined cross sectional view simply illustrating a part of an instrument lifting operation device according to a first example of the invention.
Figure 3:
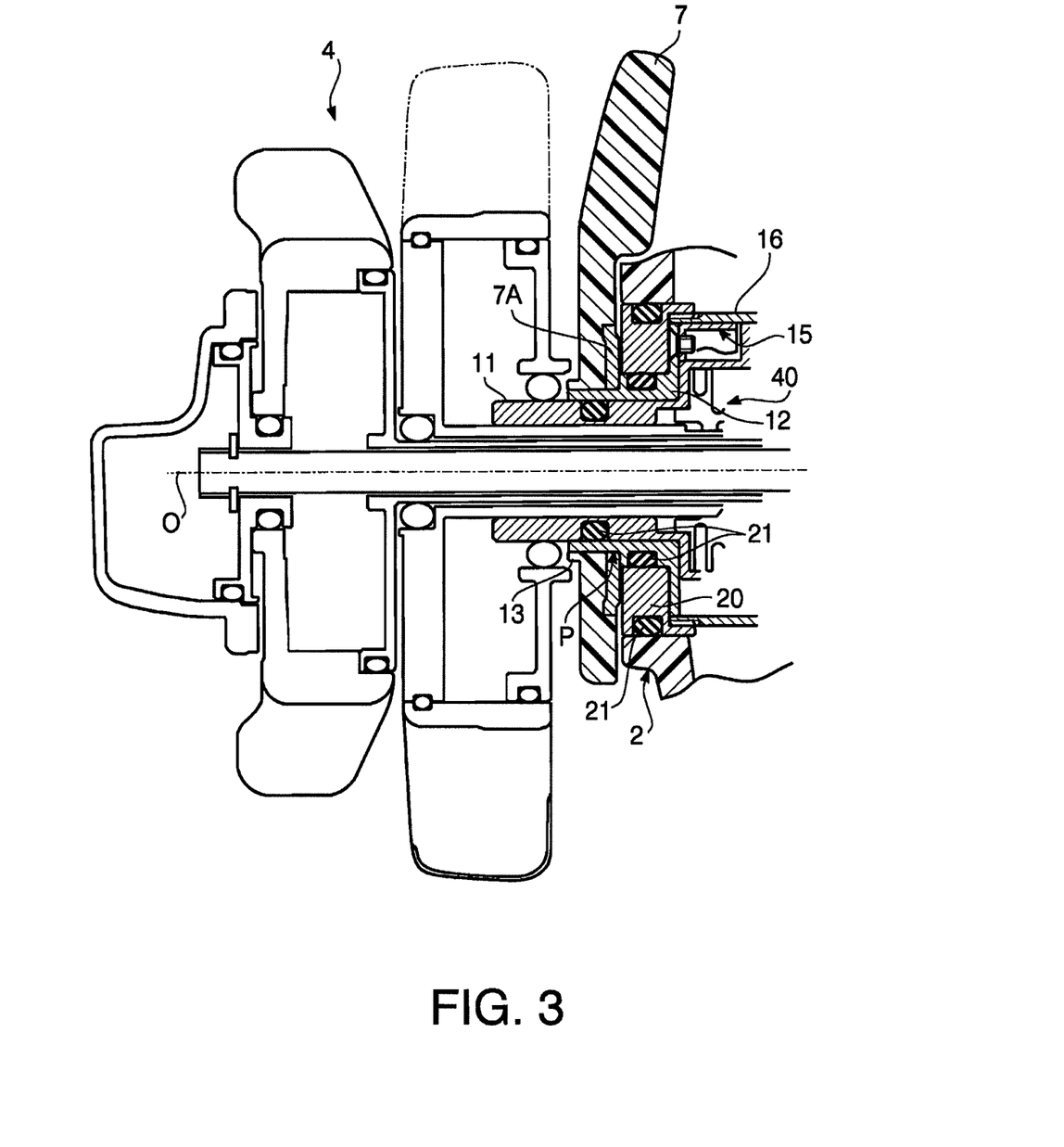
FIG. 3 is a side cross section of the instrument lifting operation device according to the first example of the invention.

FIG. 3 illustrates a first example of an instrument lifting operation device for an endoscope provided in the operation unit 2. FIG. 1 is a combined cross sectional view in which cross sections orthogonal to an axis of the instrument lifting operation device are combined. Reference symbol 11 represents a support shaft of the instrument lifting operation device, and the support shaft 11 is fixed to an fixed frame 9 provided in the operation unit 2 (see FIG. 1). The support shaft 11 is formed to have a cylindrical shape and serves also as an external bearing for the bending operation device 4.

A rotation member 12, which is rotatably fitted to an outer circumferential part of the support shaft 11, and a coupling plate 7A integrally fixed to the instrument lifting operation lever 7 are coupled to each other, at a square shaft coupling part P positioned outside of the operation unit 2, so as not to wobble in a rotational direction, and the state the rotation member 12 and the coupling plate 7A is fixed by a retaining nut 13. As a result, the instrument lifting operation lever 7 and the rotation member 12 rotate together about an axis O (i.e., a center axis of the rotation member 12).

Reference symbol 20 represents a lid which seals a hole formed in an exterior part of the operation unit 2 to allow the support shaft 11 and the rotation member 12 to pass therethrough. Around the lid 20, a plurality of O rings 21 are provided to prevent water from invading into the inside of the operation unit 2.

A spring 15 for producing the frictional resistance is attached to the rotation member 12 at a position inside of the operation unit 2. Reference symbol 16 represents a fixed wall attached fixedly to the fixed frame 9 in the operation unit 2, and has a smooth inner wall having a shape of an arc which is inwardly faced and is coaxial with the rotation member 12.

The spring 15 is attached to the rotation member 12 so that the spring 15 rotates, together with the rotation member 12 (i.e., together with the instrument lifting operation lever 7), about the axis O of the rotation member 12 in the state where the spring 15 is elastically pressed against an inner circumferential surface of the fixed wall 16.

As shown in FIG. 1, the spring 15 has a fixed end 16y fixed to the rotation member 12 and a free end 15z which is positioned oppositely to the fixed end 15y to slidably contact the circumferential surface (an inner circumferential surface in this case) of the fixed wall 16. At the free end 15z of the spring 15, a contacting projected part 15A is formed to locally project so that the contacting projected part 15A slidably contacts the inner circumferential surface of the fixed wall 16.

The contacting projected part 15A is formed to have a semicircular shape protruding toward the fixed wall 16. Since the tip of the contacting projected part 15A is elastically pressed against the inner circumferential surface of the fixed wall 16, the frictional resistance is produced at the contacting part of the contacting projected part 15A and the inner circumferential surface of the fixed wall. The contacting projected part 15A and the instrument lifting operation lever 7 are positioned substantially in the same direction when viewed from the axis O.

A wire coupling member 17 to which the proximal end of the operation wire 8 is connected is fixedly connected to the rotation member 12. By operating the instrument lifting operation lever 7, the wire coupling member 17 can be rotated about the axis O. A coupling part between the wire coupling member 17 and the operation wire 8 is formed to protrude outward from the fixed wall 16. Reference symbol 18 represents a bending operation wire.

With this configuration, when the instrument lifting operation lever 7 is manually rotated with respect to the axis O as shown by an arrow A in FIG. 1, the wire coupling member 17 rotates as shown by an arrow B, and the operation wire 8 moves forward or backward. Consequently, the instrument lifting piece 6 is driven to swing in the tip part body 5. As described above, an operation wire drawing mechanism for manually drawing the proximal end of the operation wire 8 is formed by components including the instrument lifting operation lever 7, the rotation member 12 and the wire coupling member 17.

Figure 4:
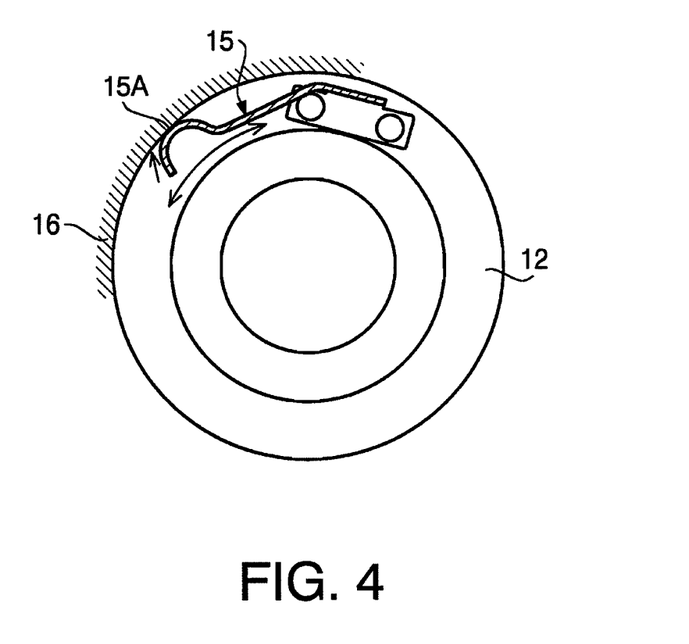
FIG. 4 is a partially enlarged front view of the instrument lifting operation device according to the first example of the invention.

As shown in FIG. 4 as an enlarged view, the contacting projected part 15A of the spring 15 is elastically pressed against the inner circumferential surface of the fixed wall 16, and therefore the contacting projected part 15A and the inner circumferential surface of the fixed wall 16 contact with each other in the state where the spring 15 is elastically deformed. As a result, the frictional resistance is produced between the contacting projected part 15A and the inner circumferential surface of the fixed wall 16. Therefore, even if the operator's finger is released from the instrument lifting operation lever 7, the operation wire 8 does not move to the tip side unless a drawing force of a certain strength or more is applied from the instrument lifting piece 6 to the operation wire 8.

As described above, a braking mechanism for restricting movement of the operation wire 8 toward the tip side by the drawing force from the instrument lifting piece 6 is configured by components including the spring 15 and the fixed wall 6. The braking mechanism (15, 16) can be arranged in space (such as peripheral space of a bending operation pulley mechanism 40 (see FIG. 3)) not interfering with other components in the operation unit 2.

Figure 5:
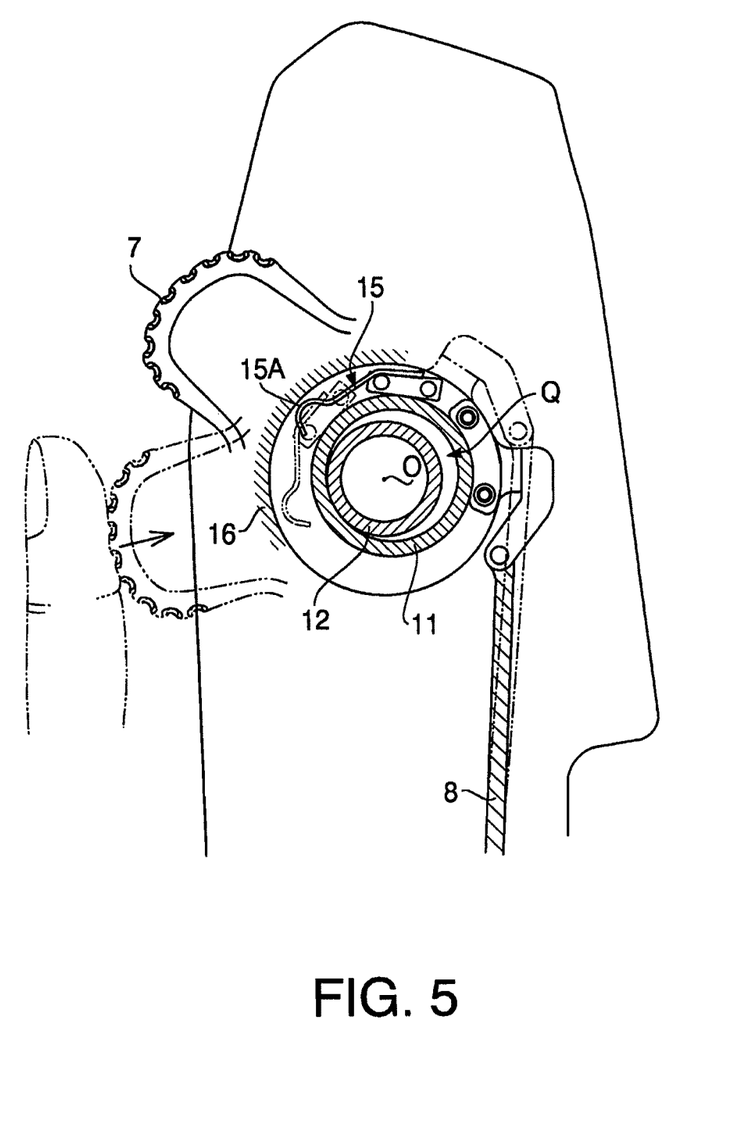
FIG. 5 is a combined cross section for explaining an operation for the instrument lifting operation device according to the first example of the invention.

It should be noted that between rotational fitting surfaces of the support shaft 11 and the rotation member 12, slight play is secured in the radial direction. As a result, as shown in FIG. 5, when the instrument lifting operation lever 7 is manually rotated, the instrument lifting operation lever 7 is pressed inward (toward the axis O) by the operator's finger, and thereby the rotation member 12 integrally provided with the instrument lifting operation lever 7 also shifts inward with respect to the support shaft 11 by an amount corresponding to the play Q. In FIG. 5, the play Q is exaggerated for convenience of explanation.

Since as described above the contacting projected part 15A of the spring 15 and the instrument lifting operation lever 7 are position in substantially the same direction when viewed from the axis O, the contacting projected part 15A moves inward by the amount corresponding to the play Q from the inner circumferential surface of the fixed wall 16.

As a result, the pressing force of the spring 15 against the inner circumferential surface of the fixed wall 16 decreases and thereby the frictional resistance between the contacting projected part 15A and the fixed wall 16 decreases, although the contacting projected part 15A does not actually move from the inner circumferential surface of the fixed wall 16 because the contacting projected part 15A is elastically pressed against the inner circumferential surface of the fixed wall 16. Therefore, the dynamic frictional resistance becomes smaller relative to the static frictional resistance, and thereby it becomes possible to manually rotate the instrument lifting operation lever 7 by a small force.

Figure 6:
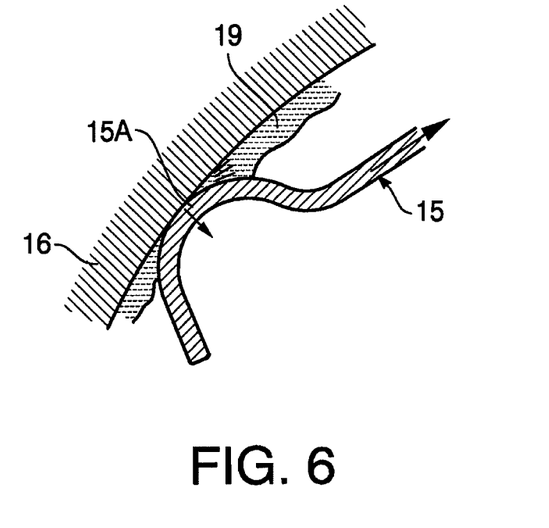
FIG. 6 is a partially enlarged front view of the instrument lifting operation device according to a second example of the invention.

FIG. 6 illustrates a second example of an instrument lifting operation device for an endoscope provided in the operation unit 2. As shown in FIG. 6, in the second example, a lubricant 19 is applied to the contacting part between the contacting projected part 15A of the spring 15 and the fixed wall 16. With this configuration, by the wedge effect where the lubricant 19 is sandwiched between the contacting projected part 15A of the spring 15 and the inner circumferential surface of the fixed wall 16, the contacting projected part 15A is lifted by ascending of pressure of an oil film on the friction surface during sliding of the contacting projected part 15A, and thereby the dynamic frictional resistance decreases.

Theoretically, the above described phenomenon is similar to a general sliding bearing, and the dynamic frictional resistance becomes smaller than the static frictional resistance at the contacting part between the contacting projected part 15A of the spring 15 and the fixed wall 16. Therefore, it becomes possible to manually rotate the instrument lifting operation lever 7 by a small force. As the lubricant 19, grease is appropriate. By using fluorinated grease, the durability can also be enhanced.

Figure 7:
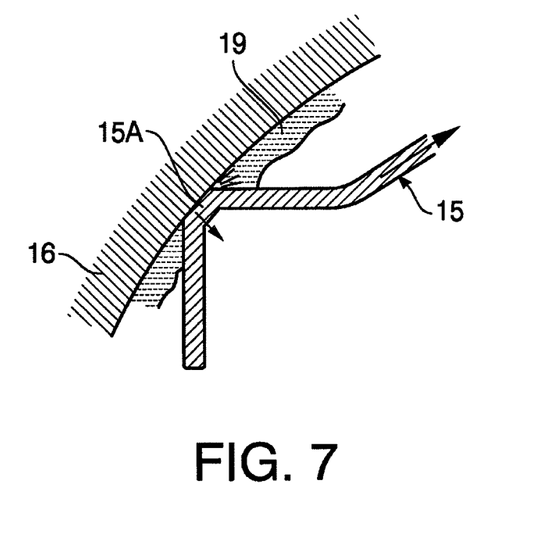
FIG. 7 is a partially enlarged front view of the instrument lifting operation device according to a third example of the invention.

FIG. 7 illustrates a third example of an instrument lifting operation device for an endoscope provided in the operation unit 2. As shown in FIG. 7, the contacting projected part 15A of the spring 15 may have a projected shape (e.g., a shape of a mound) different from the semicircular shape.

Figure 8:
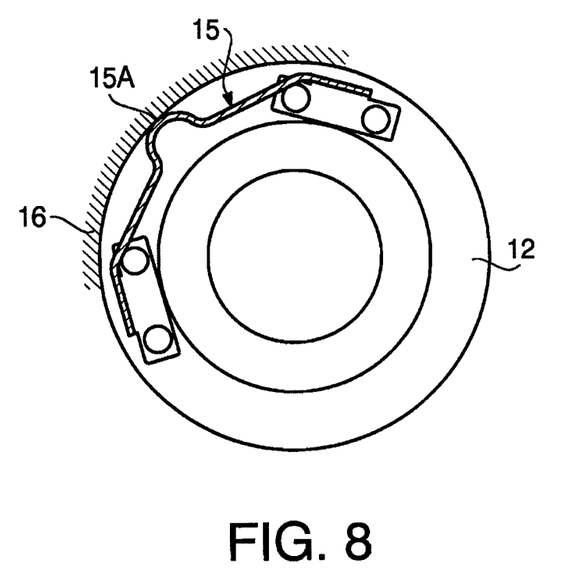
FIG. 8 is a partially enlarged front view of the instrument lifting operation device according to a fourth example of the invention.

FIG. 8 illustrates a fourth example of an instrument lifting operation device for an endoscope provided in the operation unit 2. As shown in FIG. 8, the spring 15 may be formed to have a shape of a "double-arm" arranged to be fixed at both ends. By employing such a double-arm type spring, occurrence of unnecessary deformation of the spring can be suppressed, and thereby it becomes possible to provide a suitable effect with respect to the operation stability and the durability.

Figure 9:
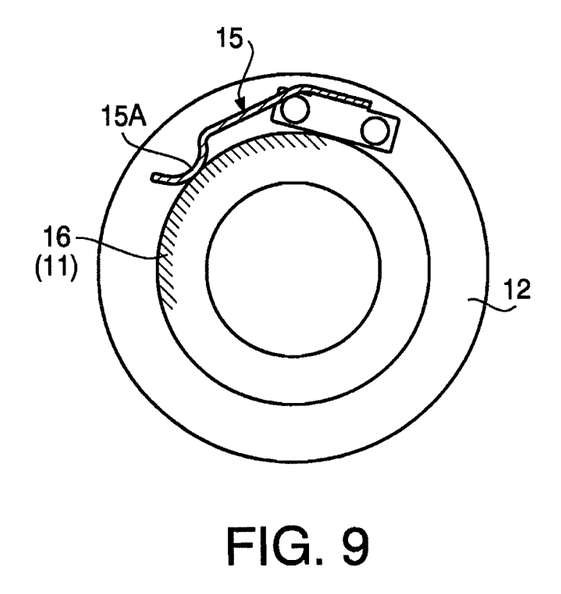
FIG. 9 is a partially enlarged front view of the instrument lifting operation device according to a fifth example of the invention.
Figure 10:
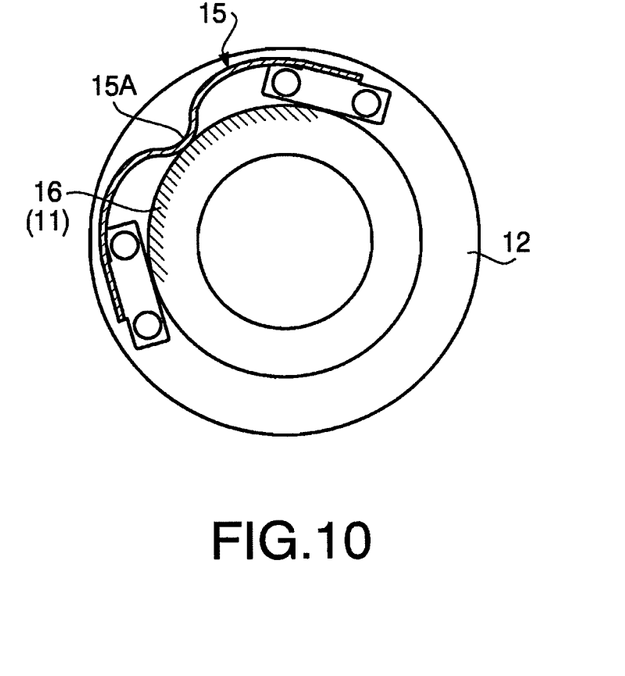
FIG. 10 is a partially enlarged front view of the instrument lifting operation device according to a sixth example of the invention.

FIGS. 9 and 10 respectively illustrate fifth and sixth examples of an instrument lifting operation device for an endoscope provided in the operation unit 2. The spring 15 shown in FIG. 9 is a single-arm type spring, and the spring shown in FIG. 10 is a double-arm type spring. As shown in FIGS. 9 and 10, the contacting projected part 15A of the spring 15 may be formed to contact the outer circumferential surface of the fixed wall 16. In this case, since the support shaft 11 is able to serve also as the fixed wall 16, it becomes possible to downsize the projector.

Although the present invention has been described in considerable detail with reference to certain preferred embodiments thereof, other embodiments are possible.

This application claims priority of Japanese Patent Application No. P2009-225832, filed on Sep. 30, 2009. The entire subject matter of the application is incorporated herein by reference.

What is claimed is:

1. An instrument lifting operation device for an endoscope for remotely controlling, from an operation unit connected to a proximal end of an insertion unit, an instrument lifting piece movably arranged on a tip side of the insertion unit of the endoscope, comprising:

an operation wire drawing mechanism configured to draw, in response to a manual operation, an proximal end of an operation wire whose tip is connected to the instrument lifting piece; and a braking mechanism configured to restrict movement of the operation wire toward the tip side by a drawing force applied to the operation wire from the instrument lifting piece, wherein the operation wire drawing mechanism and the braking mechanism are arranged in the operation unit of the endoscope, wherein the operation wire drawing mechanism includes:

an instrument lifting operation member which is rotatable about an axis; and a wire coupling member to which the proximal end of the operation wire is connected, the wire coupling member being arranged to be rotated about the axis by the instrument lifting operation member, wherein the braking mechanism includes:

a fixed wall fixedly arranged in the operation unit to have a shape of an arc having a center corresponding to the axis and a spring arranged to be able to rotate about the axis together with the instrument lifting operation member in a state where the spring is elastically pressed against an inner circumferential surface of the fixed wall, the inner circumferential surface of the fixed wall having a constant diameter, wherein when the instrument lifting operation member is operated to rotate about the axis, the wire coupling member rotates about the axis and the operation wire moves forward and backward in a state where the spring contacts and slides on the inner circumferential surface of the fixed wall to generate frictional resistance at a contacting part of the spring and the inner circumferential surface of the fixed wall, and the spring including:
  a fixed end fixed to a rotation member arranged to rotate about the axis together with the instrument lifting operation member; and
  a free end which contacts and slides on the inner circumferential surface of the fixed wall,
  the free end including a contacting projection having a semicircular shape protruding toward the inner circumferential surface of the fixed wall so as to contact and slide on the inner circumferential surface of the fixed wall.

2. The instrument lifting operation device according to claim 1, wherein the instrument lifting operation member and the contacting projection of the spring are arranged substantially in a same direction when viewed from a position of the axis.

3. The instrument lifting operation device according to claim 1, wherein a lubricant is applied to the contacting part of the spring and the inner circumferential surface of the fixed wall.

4. The instrument lifting operation device according to claim 3, wherein the lubricant is grease.

5. The instrument lifting operation device according to claim 1, wherein a frictional braking resistance is produced as a contacting part of the contacting projection slides on an inner circumferential surface of the fixed wall.

6. The instrument lifting operation device according to claim 1, wherein the spring extends only partially around the rotation member in a circumferential direction.

7. The instrument lifting operation device according to claim 1, wherein an extending direction of the spring, which is defined from the fixed end of the spring to the free end of the spring, coincides with a circumferential direction of the rotation member.

8. An endoscope, comprising:
an insertion unit;
an operation unit connected to a proximal end of the insertion unit; and
an instrument lifting operation device configured to remotely control, from the operation unit, an instrument lifting piece movably arranged on a tip side of the insertion unit, wherein the instrument lifting operation device includes:

an operation wire drawing mechanism configured to draw, in response to a manual operation, an proximal end of an operation wire whose tip is connected to the instrument lifting piece; and a braking mechanism configured to restrict movement of the operation wire toward the tip side by a drawing force applied to the operation wire from the instrument lifting piece, wherein the operation wire drawing mechanism and the braking mechanism are arranged in the operation unit, wherein the operation wire drawing mechanism includes:

an instrument lifting operation member which is rotatable about an axis; and a wire coupling member to which the proximal end of the operation wire is connected, the wire coupling member being arranged to be rotated about the axis by the instrument lifting operation member, wherein the braking mechanism includes:

a fixed wall fixedly arranged in the operation unit to have a shape of an arc having a center corresponding to the axis and a spring arranged to be able to rotate about the axis together with the instrument lifting operation member in a state where the spring is elastically pressed against an inner circumferential surface of the fixed wall, the inner circumferential surface of the fixed wall having a constant diameter, wherein when the instrument lifting operation member is operated to rotate about the axis, the wire coupling member rotates about the axis and the operation wire moves forward and backward in a state where the spring contacts and slides on the inner circumferential surface of the fixed wall to generate frictional resistance at a contacting part of the spring and the inner circumferential surface of the fixed wall, the spring including:
  a fixed end fixed to a rotation member arranged to rotate about the axis together with the instrument lifting operation member; and
  a free end which contacts and slides on the inner circumferential surface of the fixed wall,
  the free end including a contacting projection having a semicircular shape protruding toward the inner circumferential surface of the fixed wall so as to contact and slide on the inner circumferential surface of the fixed wall.

9. The endoscope according to claim 8, wherein the instrument lifting operation member and the contacting projection of the spring are arranged substantially in a same direction when viewed from a position of the axis.

10. The endoscope according to claim 8, wherein a lubricant is applied to the contacting part of the spring and the inner circumferential surface of the fixed wall.

11. The endoscope according to claim 10, wherein the lubricant is grease.

12. The endoscope according to claim 8, wherein a frictional braking resistance is produced as a contacting part of the contacting projection slides on an inner circumferential surface of the fixed wall.

13. The endoscope according to claim 8, wherein the spring extends only partially around the rotation member in a circumferential direction.

14. The endoscope according to claim 8, wherein an extending direction of the spring, which is defined from the fixed end of the spring to the free end of the spring, coincides with a circumferential direction of the rotation member.

* * * * *